United States Patent
Marliere et al.

(10) Patent No.: US 7,399,611 B2
(45) Date of Patent: Jul. 15, 2008

(54) DESCENDANTS OF BACTERIA DEVOID OF N TERMINAL FORMYLATION USEFUL FOR THE PRODUCTION OF PROTEINS AND PEPTIDES

(75) Inventors: Philippe Marliere, Paris (FR); Rupert Mutzel, Berlin (DE); Didier Mazel, Suresnes (FR)

(73) Assignee: Institut Pasteur, Paris (FR)

( * ) Notice: Subject to any disclaimer, the term of this patent is extended or adjusted under 35 U.S.C. 154(b) by 242 days.

(21) Appl. No.: 11/176,368

(22) Filed: Jul. 8, 2005

(65) Prior Publication Data

US 2006/0014250 A1 Jan. 19, 2006

Related U.S. Application Data

(62) Division of application No. 10/189,505, filed on Jul. 8, 2002, now Pat. No. 6,962,807.

(60) Provisional application No. 60/303,065, filed on Jul. 6, 2001.

(51) Int. Cl.
*C12P 21/02* (2006.01)
(52) U.S. Cl. .................................. 435/69.1; 435/252.33
(58) Field of Classification Search ....................... None
See application file for complete search history.

(56) References Cited

U.S. PATENT DOCUMENTS 6,962,807 B2 * 11/2005 Marliere et al. ......... 435/252.33

OTHER PUBLICATIONS

Thierry Meinnel, et al., "Characterization of the Thermus thermophilus Locus Encoding Peptide Deformylase and Methionyl-tRNA$^{MET}$ Formyltransferase," Journal of Bacteriology (1994). vol. 176, No. 23, pp. 7387-7390.

Thierry Meinnel, et al., "Structure-Function Relationships within the Peptide Deformylase Family. Evidence for a Conserved Architecture of the Active Site Involving Three Conserved Motifs and a Metal Ion," J. Biol. Mol. (1997), vol. 267, pp. 749-761.

Andreas Kreusch, et al., "Structure Analysis of Peptide Deformylases from *Streptococcus pnewmoniae, Straphylococcus aureaus, Thermotoga maritima and Pseudomonas aeruginosa*: Snapshots of the Oxygen Sensitivity of Peptide Deformylase," J. Mol. Biol. (2003), vol. 330, pp. 309-321.

Didier Mazel, et al., "A Survey of Polypeptide Deformylase Function Throughout the Eubacterial Lineage," J. Mol. Biol. (1997), vol. 266, pp. 939-949.

M. Vulic, et al., Proceedings of the National Academy of Sciences of the United States of American, vol. 96, No. 13, pp. 7348-7351, XP-002220212, "Mutation, Recombination, and Incipient Speciation of Bacteria in the Laboratory", Jun. 22, 1999.

D. Mazel, et al., EMBO Journal, vol. 13, No. 4, pp. 914-923, XP-002043973, "Genetic Characterization of Polypeptide Defomylase, A Distinctive Enzyme of Eubacterial Translation", Feb. 15, 1994.

Mazel et al. Genetic characterization of polypeptide deformylase a distinctive enzyme of eubacterial translation. EMBO Journal, vol. 13, No. 4, 1994, pp. 914-923.

Marolewski et al. Cloning and characterization of a new pruine blosynthetic enzyme Biochemistry, vol. 33, No. 9, pp. 2531-2537, 1994.

* cited by examiner

*Primary Examiner*—James S Ketter
(74) *Attorney, Agent, or Firm*—Oblon, Spivak, McClelland, Maier & Neustadt, P.C.

(57) ABSTRACT

Eubacterial cells which produce non-formylated proteins, polypeptides and/or peptides and methods for making such non-formylated products. The eubacterial cells may be produced by inactivating or deleting the def (deformylase) and/or fmt (Met-tRNA transformylase) gene(s) from the def-fmt operon of the corresponding wild-type strain.

19 Claims, 5 Drawing Sheets

SEQUENCE LISTING

<160> NUMBER OF SEQ ID NOS: 4

<210> SEQ ID NO 1
<211> LENGTH: 169
<212> TYPE: PRT
<213> ORGANISM: Escherichia coli

<400> SEQUENCE: 1

Met Ser Val Leu Gln Val Leu His Ile Pro Asp Glu Arg Leu Arg Lys
1               5                   10                  15

Val Ala Lys Pro Val Glu Glu Val Asn Ala Glu Ile Gln Arg Ile Val
            20                  25                  30

Asp Asp Met Phe Glu Thr Met Tyr Ala Glu Gly Ile Gly Leu Ala
        35                  40                  45

Ala Thr Gln Val Asp Ile His Gln Arg Ile Ile Val Ile Asp Val Ser
    50                  55                  60

Glu Asn Arg Asp Glu Arg Leu Val Leu Ile Asn Pro Glu Leu Leu Glu
65                  70                  75                  80

Lys Ser Gly Glu Thr Gly Ile Glu Glu Gly Cys Leu Ser Ile Pro Glu
                85                  90                  95

Gln Arg Ala Leu Val Pro Arg Ala Glu Lys Val Lys Ile Arg Ala Leu
            100                 105                 110

Asp Arg Asp Gly Lys Pro Phe Glu Leu Glu Ala Asp Gly Leu Leu Ala
        115                 120                 125

Ile Cys Ile Gln His Glu Met Asp His Leu Val Gly Lys Leu Phe Met
    130                 135                 140

Asp Tyr Leu Ser Pro Leu Lys Gln Gln Arg Ile Arg Gln Lys Val Glu
145                 150                 155                 160

Lys Leu Asp Arg Leu Lys Ala Arg Ala
                165

<210> SEQ ID NO 2
<211> LENGTH: 510
<212> TYPE: DNA
<213> ORGANISM: Escherichia coli

<400> SEQUENCE: 2
atgtcagttt tgcaagtgtt acatattccg gacgagcggc ttcgcaaagt tgctaaaccg      60
gtagaagaag tgaatgcaga aattcagcgt atcgtcgatg atatgttcga gacgatgtac     120
gcagaagaag gtattggcct ggcggcaacc caggttgata tccatcaacg tatcattgtt     180
attgatgttt cggaaaaccg tgacgaacgg ctagtgttaa tcaatccaga gcttttagaa     240
aaaagcggcg aaacaggcat tgaagaaggt tgcctgtcga tccctgaaca acgtgcttta     300
gtgccgcgcg cagagaaagt taaaattcgc gcccttgacc gcgacggtaa accatttgaa     360
ctggaagcag acggtctgtt agccatctgt attcagcatg agatggatca cctggtcggc     420
aaactgttta tggattatct gtcaccgctg aaacaacaac gtattcgtca gaaagttgaa     480
aaactggatc gtctgaaagc ccgggcttaa                                      510

<210> SEQ ID NO 3
<211> LENGTH: 315
<212> TYPE: PRT
<213> ORGANISM: Escherichia coli

<400> SEQUENCE: 3

```
Met Ser Glu Ser Leu Arg Ile Ile Phe Ala Gly Thr Pro Asp Phe Ala
1               5                   10                  15

Ala Arg His Leu Asp Ala Leu Leu Ser Ser Gly His Asn Val Val Gly
            20                  25                  30

Val Phe Thr Gln Pro Asp Arg Pro Ala Gly Arg Gly Lys Lys Leu Met
                35                  40                  45

Pro Ser Pro Val Lys Val Leu Ala Glu Glu Lys Gly Leu Pro Val Phe
        50                  55                  60

Gln Pro Val Ser Leu Arg Pro Gln Glu Asn Gln Gln Leu Val Ala Glu
65                  70                  75                  80

Leu Gln Ala Asp Val Met Val Val Ala Tyr Gly Leu Ile Leu Pro
                85                  90                  95

Lys Ala Val Leu Glu Met Pro Arg Leu Gly Cys Ile Asn Val His Gly
                100                 105                 110

Ser Leu Leu Pro Arg Trp Arg Gly Ala Ala Pro Ile Gln Arg Ser Leu
            115                 120                 125

Trp Ala Gly Asp Ala Glu Thr Gly Val Thr Ile Met Gln Met Asp Val
        130                 135                 140

Gly Leu Asp Thr Gly Asp Met Leu Tyr Lys Leu Ser Cys Pro Ile Thr
145                 150                 155                 160

Ala Glu Asp Thr Ser Gly Thr Leu Tyr Asp Lys Leu Ala Glu Leu Gly
                165                 170                 175

Pro Gln Gly Leu Ile Thr Thr Leu Lys Gln Leu Ala Asp Gly Thr Ala
            180                 185                 190

Lys Pro Glu Val Gln Asp Glu Thr Leu Val Thr Tyr Ala Glu Lys Leu
        195                 200                 205

Ser Lys Glu Glu Ala Arg Ile Asp Trp Ser Leu Ser Ala Ala Gln Leu
210                 215                 220

Glu Arg Cys Ile Arg Ala Phe Asn Pro Trp Pro Met Ser Trp Leu Glu
225                 230                 235                 240

Ile Glu Gly Gln Pro Val Lys Val Trp Lys Ala Ser Val Ile Asp Thr
                245                 250                 255

Ala Thr Asn Ala Ala Pro Gly Thr Ile Leu Glu Ala Asn Lys Gln Gly
            260                 265                 270

Ile Gln Val Ala Thr Gly Asp Gly Ile Leu Asn Leu Leu Ser Leu Gln
        275                 280                 285

Pro Ala Gly Lys Lys Ala Met Ser Ala Gln Asp Leu Leu Asn Ser Arg
290                 295                 300

Arg Glu Trp Phe Val Pro Gly Asn Arg Leu Val
305                 310                 315
```

<210> SEQ ID NO 4
<211> LENGTH: 948
<212> TYPE: DNA
<213> ORGANISM: Escherichia coli

<400> SEQUENCE: 4

```
gtgtcagaat cactacgtat tattttttgcg ggtacacctg actttgcagc gcgtcatctc    60
gacgcgctgt tgtcttctgg tcataacgtc gttggcgtgt tcacccagcc agaccgaccg   120
gcaggacgcg gtaaaaaact gatgcccagc ccggttaaag ttctggctga ggaaaaaggt   180
ctgcccgttt ttcaacctgt ttccctgcgt ccacaagaaa accagcaact ggtcgccgaa   240
ctgcaggctg atgttatggt cgtcgtcgcc tatggtttaa ttctgccgaa agcagtgctg   300
gagatgccgc gtcttggctg tatcaacgtt catggttcac tgctgccacg ctggcgcggt   360
```

```
gctgcaccaa tccaacgctc actatgggcg ggtgatgcag aaactggtgt gaccattatg      420
caaatggatg tcggtttaga caccggtgat atgctctata agctctcctg cccgattact      480
gcagaagata ccagtggtac gctgtacgac aagctggcag agcttggccc acaagggctt      540
atcaccacgt tgaaacaact ggcagacggc acggcgaaac cagaagttca ggacgaaact      600
cttgtcactt acgccgagaa gttgagtaaa gaagaagcgc gtattgactg gtcactttcg      660
gcagcacagc ttgaacgctg cattcgcgct ttcaatccat ggccaatgag ctggctggaa      720
attgaaggac agccggttaa agtctggaaa gcatcggtca ttgatacggc aaccaacgct      780
gcaccaggaa cgatccttga agccaacaaa caaggcattc aggttgcgac tggtgatggc      840
atcctgaacc tgctctcgtt acaacctgcg ggtaagaaag cgatgagcgc gcaagacctc      900
ctgaactctc gtcgggaatg gtttgttccg ggcaaccgtc tggtctga                  948
```

DESCENDANTS OF BACTERIA DEVOID OF N TERMINAL FORMYLATION USEFUL FOR THE PRODUCTION OF PROTEINS AND PEPTIDES

CROSS REFERENCE TO A RELATED APPLICATION

This application claims priority to U.S. application Ser. No. 10/189,505, filed Jul. 8, 2002 now U.S. Pat. No. 6,962,807 (now allowed) and to U.S. Provisional Application 60/303,065, which was filed on Jul. 6, 2001.

FIELD OF THE INVENTION

The present invention is useful for production of recombinant proteins in eubacterial hosts. An eubacterial host defective in the genes for Met-tRNAi transformylase and polypeptide deformylase is described which grows in minimal and complex nutrient media at 30° C., 37° C. and 42° C. with near wild-type rate. In this *eubacterium* protein synthesis does not require N-formyl methionine as the initiator methionine, protein synthesis instead is initiated with unmodified methionine. The absence of peptides which retain N-formyl methionine in this *eubacterium* makes it particularly suited for the expression of recombinant proteins for pharmaceutical use.

BACKGROUND OF THE INVENTION

In eubacteria, peptide synthesis is initiated at methionine start codons which are read by N-formyl methionine tRNA. Prior to translation initiation the methionyl moiety of the charged tRNA is N-formylated by the action of Met-tRNAi transformylase (E.C.2.1.2.9). The N-formyl group is removed from the native protein by polypeptide deformylase (E.C. 3.5.127), and the initiator methionine can then be cleaved off by methionine aminopeptidase, completing the primer methionine cycle. In contrast, archaea and eukaryotes have a primer methionine cycle devoid of N-formylating and deformylating activities (for review see Mazel, D., Pochet, S. and Marliere, P.: Genetic characterization of polypeptide deformylase, a distinctive enzyme of eubacterial translation. EMBO J. 13 (1994) 914-923, and Mazel et al., 1996).

Expression of eukaryotic proteins in eubacterial hosts often results in the production of recombinant proteins that retain an N-terminal formylmethionyl residue (examples include bovine somatotropin (Bogosian, G., et al., (1989) Biosynthesis and incorporation into protein of norleucine by *Escherichia coli* J. Biol. Chem. 264:531-539); eel growth hormone (Sugimoto, S., Yamaguchi, K. and Yokoo, Y.: Isolation and characterization of recombinant eel growth hormone expressed in *Escherichia coli*. J. Chromatog. 515 (1990) 483-494); human granulocyte colony-stimulating factor (Clogston, C. L., Hsu, Y. R, Boone, T. C. and Lu, H. S.: Detection and quantitation of recombinant granulocyte colony-stimulating factor charge isoforms: comparative analysis by cationic-exchange chromatography, isoelectric focusing gel electrophoresis, and peptide mapping. Anal. Biochem. 202 (1992) 375-383); bovine fatty acid-binding protein (Specht, B., Oudenampsen-Kruger, E., Ingendoh, A., Hillenkamp, F., Lezius, A. G. and Spener, F.: N-terminal variants of fatty acid-binding protein from bovine heart overexpressed in *Escherichia coli*. J. Biotechnol. 33 (1994) 259-269); bovine cytochrome P450 (Dong et al FASEB J. 9 (1995) A1486); Methanothermus fervidus histone A (Sandman, K., Grayling, R. A., and Reeve, J. N. Improved N-terminal Processing of Recombinant Proteins Synthesized in *Escherichia coli*. Biotechnology 13 (1995) 504-506); human interleukin-5 (Rose, K., Regarney, P., Anderegg, R, Wells, T., Proudfoot, A., Human interleukin-5 expressed in *Escherichia coli* has N-terminal modifications. Biochem J. 286 (1992) 825-828); human parathyroid hormone (Rabbani, S. A., Yasuda T., Bennett H. P. J., Sung, W. L. Zahab, D. M., Tam, C. S. Goltman, D., and Hendy, G. N. Recombinant Human Parathyroid Hormone Synthesized in *Escherichia coli*. Journal of Biological Chemistry 263:3 (1988) 1307-1313; Hogset, A., Blingsmo, O. R., Gaurvk V. T., Saether, O., Jacobsen, P. B., Gordeladzo, J. O., Alestrom, P. and Gautvik, K. M. Expression of Human Parathyroid Hormone In *Escherichia coli* Biochemical and Biophysical Research Communications 166:1 (1990) 50-60); human gamma-interferon (Honda, S., Asano, T., Kajio, T., and Nishimura, O. *Escherichia coli*-Derived Human Interferon-.gamma. with Cys-Tyr-Cys at the N-Terminus is Partially Nα-Acylated. Archives of Biochemistry and Biophysics 269 (1989) 612-622)). In addition retention of N-formyl methionine has been found in endogeneous *E. coli* proteins (Hauschild-Rogat, P. N-formylmethionine as a N-terminal group of *E. coli* ribosomal protein. Mol. Geri. Genet. 102 (1968) 95-101, Marasco, W. A., Phan, S. H., Kruusch, H., Showell, H. J., Feltner, D. E., Nairn, R, Becker, E. L. and Ward, P. A.: Purification and identification of formyl-methionyl-leucyl-phenylalanine as the major peptide neutrophil chemotaetic factor produced by *Escheriehia coli*. J. Biol. Chem. 259 (1984) 5430-5439; Milligan, D. L. and Koshland, Jr., D. E.: The amino terminus of the aspartate chemoreceptor is formylmethionine. J. Biol. Chem. 265 (1990) 4455-4460). Since N-formylated peptides are a major indicator of eubacterial infections for the mammalian immune system and are highly immunogenic, incomplete deformylation precludes; for example, the use of N-formylated preparations for therapeutic purposes. Several approaches to circumvent this problem have been proposed, e.g., expression in the presence of trimethoprim and thymidine (Sandman et al., 1995), overexpression of peptide deformylase in the host (Warren, W. C., Bentle, K. A., Schlittler, M. R, Schwane, A. C., O'Neil, J. P. and Bogosian, G. (1996): increased production of peptide deformylase eliminates retention of formylmethionine in bovine somatotropin overproduced in *Escherichia coli*. Gene 174, 235-23), expression as a protein fusion either with an N-terminal peptide that can be removed in vitro by a specific protease or with an N-terminal leader peptide which is cleaved during transport of the nascent protein in a non-cytoplasmatic compartment. Finally, the N-formyl group may also be removed by mild acid hydrolysis, or the fraction of the protein retaining N-formyl methionine may be separated from the correctly processed protein by purification procedures.

Each of these approaches has significant disadvantages. Addition of trimethoprim and thymidine is costly, requires manipulation of the culture that will express the recombinant protein, and may slow down growth of the host. Overexpression of peptide deformylase requires a stable plasmid construct in the host that has to be selected for; moreover, deformylation may be less than 100% effective. Expression of fusion proteins requires exact molecular constructions; chemical hydrolysis with acid may cause damage to the rest of the protein. Finally, none of these approaches guarantees a final preparation that is absolutely free of N-formylated peptides derived either from the recombinant protein or from contaminations with endogeneous host peptides.

SUMMARY OF THE INVENTION

The present invention is useful for production of recombinant proteins in eubacterial hosts. An eubacterial host defective in the genes for Met-tRNAi transformylase and polypeptide deformylase is described which grows in minimal and complex nutrient media at 30° C., 37° C. and 42° C. with near wild-type rate. In this *eubacterium* protein synthesis does not require N-formyl methionine as the protein initiator protein synthesis instead being initiated with unmodified methionine. The absence of peptides which retain N-formyl methionine in this *eubacterium* makes it particularly suited for the expression of recombinant proteins for pharmaceutical use.

The present invention relates to the use of a bacterial strain lacking of transformylase and deformylase activity for the production of non formylated peptides or proteins and also the selection of a mutant bacteria which is not spontaneously reversible to the wild type for a formylase and deformylase activities but has a doubling generation time similar to the growth rate of the wild type bacteria.

More particularly the invention provides the use of a bacterial strain lacking of deformylase and/or transformylase activities characterized in that it is non reversible for the deformylase and/or transformylase activities The invention also provides the use of the bacterial strain according to the invention characterized in that it develops at a temperature of 37° C.

The invention further relates the use of a bacterial strain according to the invention characterized in that the bacteria is *E. coli*.

The invention also provides bacteria strain lacking of the protein deformylation and/or transformylation activity characterized in that:

said bacteria is not able to revert spontaneously for these activities, the growth rate of said bacteria is at least equivalent to the wild type growth rate.

The invention is also concerned with the use of the bacteria according to the invention for production of nonformylated homologous or heterologous peptides or proteins.

The invention also relates to a preparation process of peptides or proteins comprising the following steps:

a) culture of the bacteria according to the invention, b) transforming the bacteria according to step a) with a plasmid or a vector comprising an insert containing a polynucleotide coding homologous or heterologous peptide or protein, c) production of the peptide or the protein by the bacteria, and d) optionally, separation of the peptide or protein of interest from the bacterial culture.

Another object of the invention concerns a process according to the invention in which the bacteria comprises a polynucleotide coding for a mutator allele and a process according the invention in which the bacteria mutator phenotype has been complemented or the mutator allele has been replaced by the wide type allele.

The invention also concerned a purified polynucleotide comprising a gene coding for a mutator allele and contained in the bacteria strain according to the invention and a purified polynucleotide according to the invention, in which the mutator phenotype has been complemented or the mutator allele has been replaced by the wild type allele.

The invention further relates to an *E. coli* bacterial strain γ 2045 culture deposited at the CNCM (Collection Nationale de Cultures de Microorganismes), Institut Pasteur, 25 rue du Dr Roux, Paris CEDEX 15, France, on Jul. 5, 2001 under accession number I-2694.

Another aspect of the invention is directed to a process for the selection of mutants of a bacteria according to the invention characterized by the culture under continuous proliferation conditions of said mutants and separation of the mutant of interest from the static bacteria.

The invention is also concerned with a purified protein obtained after the expression of the heterologous or homologous insert of interest and deprived of formyl residue.

Other objects and advantages of the present invention will be apparent upon reading the following non restrictive detailed description made with reference to the accompanying drawing.

BRIEF DESCRIPTION OF THE DRAWINGS

FIG. 2: In vivo evolution of a D(def-fmt) mutant under permanent proliferation.

FIG. 4: Emergence and selection of adhesive variants in a conventional turbidostat, and counter-selection of adhesive variants by Evologic's process. Starting at point 1, adhesive variants were allowed to compete with cells in suspension, periodic destruction of static variants was re-established at point 3.

DETAILED DESCRIPTION OF THE INVENTION

Figures 1A, 1B:
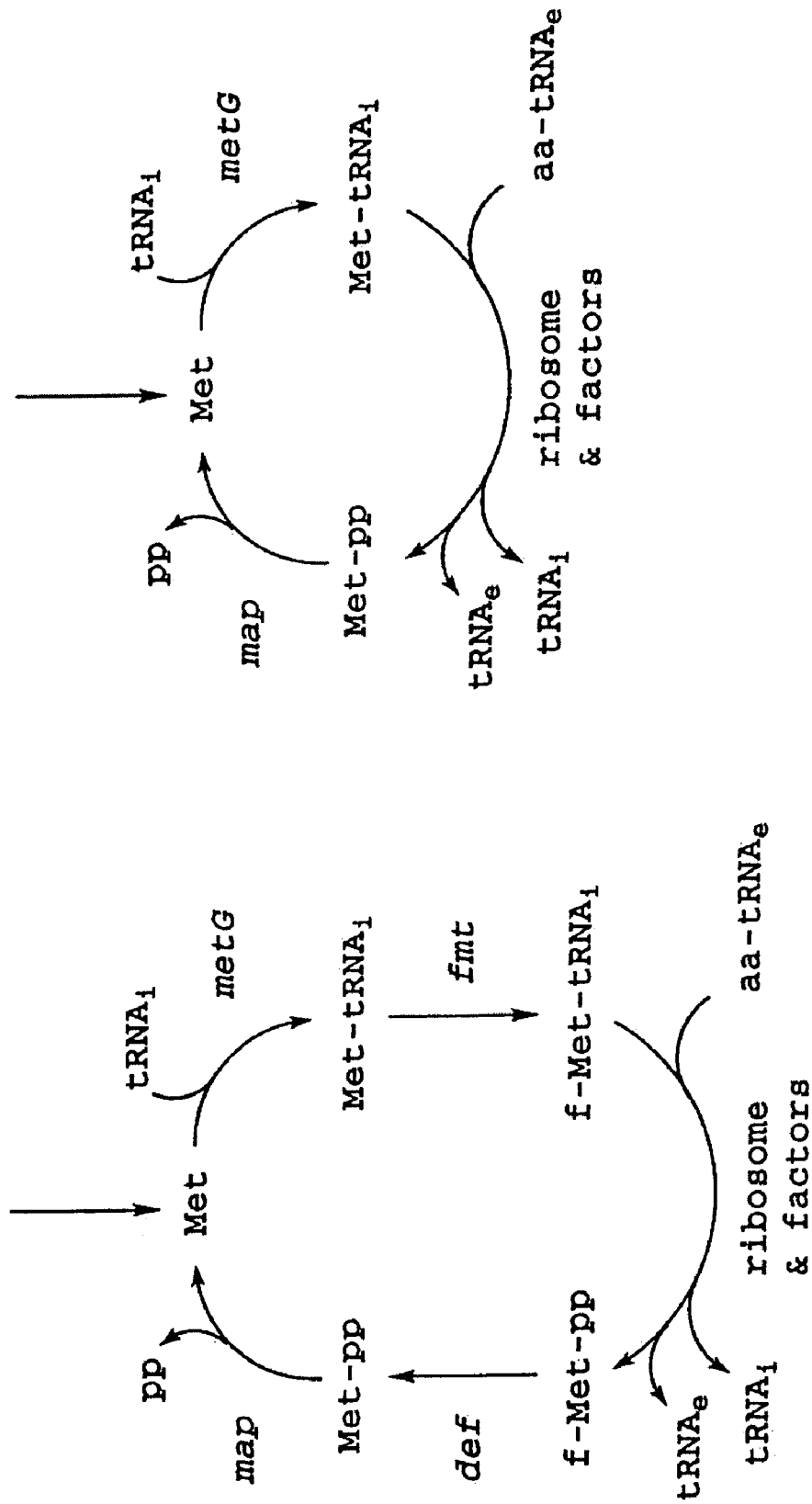
FIG. 1: The primer methionine cycle in eubacteria (1*a*) and archaea and eukaryotes (1*b*). metG, met-tRNA synthetase; fmt, met-tRNAi transformylase; def, polypeptide deformylase; map, methionine aminopeptidase; aa, amino acid; f, formyl; pp, polypeptide. Modified after (Mazel, D., Pochet, S. and Marliere, P. (1994): Genetic characterization of polypeptide deformylase, a distinctive enzyme of eubacterial translation. EMBO J. 13, 914-923).

PEPTIDE: includes any natural or synthetic compounds containing two or more amino acids. Therefore, it comprises proteins, glycoproteins, and protein fragments derived from pathogenic organisms such as viruses, bacteria, parasites and the like, or proteins isolated from normal or pathogenic tissues, such as cancerous cells. It also includes proteins and fragments thereof produced by recombinant means that has been associated or not with other peptides coding for tumoral, viral, bacterial or fungic epitopes for forming a fusion protein.

POLYNUCLEOTIDE: any DNA, RNA sequence or molecule having one nucleotide or more, including nucleotide sequences encoding a complete gene. The term is intended to encompass all nucleic acids whether occurring naturally or non naturally in a particular cell, tissue or organism. This includes DNA and fragments thereof, RNA and fragments thereof, cDNAs and fragments thereof, expressed sequence tags, artificial sequences including randomized artificial sequences.

VECTOR: a self replicating RNA or DNA molecule which can be used to transfer an RNA or DNA segment from one organism to another. Vectors are particularly useful for manipulating genetics constructs and different vectors may have properties particularly appropriate to express proteins in a recipient during cloning procedures and may comprise different selectable markers. Bacterial plasmids are commonly used as vectors.

The present invention describes an *E. coli* strain with a primer methionine cycle similar to that in eukaryotic cells. This strain no longer harbors the def fmt operon encoding Met-tRNAi transformylase and polypeptide deformylase and thus can not N-formylate Met-tRNAi. Removal of N-formyl groups from expressed proteins by any of the techniques described above is thus no longer required.

The fmt and def genes from *E. coli* were previously isolated (Guillon, J. M., Mechulam, Y., Schmitter, J. M., Blanquet, S. and Fayat, G.: Disruption of the gene for Met-tRNA-Net formyltransferase severely impairs growth of *Escherichia coli. J. Bacteriol.* 174 (1992) 4294-4301; Mazel, D., Pochet, S. and Marliere, P.: Genetic characterization of polypeptide deformylase, a distinctive enzyme of eubacterial translation. EMBO J. 13 (1994) 914-923) (def amino acid sequence is shown in SEQ ID NO: 1, def nucleotide sequence is shown in SEQ ID NO: 2; frit amino acid sequence is shown in SEQ ID NO: 3, and fmt nucleotide sequence is shown in SEQ ID NO: 4) and shown to be highly conserved among eubacteria (Mazel, D., Pochet, S. and Marliere, P.: Genetic characterization of polypeptide deformylase, a distinctive enzyme of eubacterial translation. EMBO J. 13 (1994) 914-923). Deletion mutants for either the fmt gene (Guillon, J. M., Mechulam, Y., Schmitter, J. M., Blanquet, S. and Fayat, G.: Disruption of the gene for Met-tRNA-Net formyltransferase severely impairs growth of *Escherichia coli*. J. Bacteriol. 174 (1992) 4294-4301) or the entire def-fmt operon (Mazel, D., Pochet, S. and Marliere, P.: Genetic characterization of polypeptide deformylase, a distinctive enzyme of eubacterial translation. EMBO J. 13 (1994) 914-923, D[def-fmt]) were created. The resulting mutants were reported to be severely impaired in growth. The fmt mutant has an 8.61-fold decreased growth rate at 37° C. in rich medium and does not grow at 42° C. (Guillon, J. M., Mechulam, Y., Schmitter, J. M., Blanquet, S. and Fayat, G.: Disruption of the gene for Met-tRNA-Net formyltransferase severely impairs growth of *Escherichia coli*. J. Bacteriol. 174 (1992) 4294-4301). The def-fmt mutant has a similarly decreased growth rate in minimal medium at 37° C., and growth is completely impaired in this medium at 42° C. (Mazel, D., Pochet, S. and Marliere, P.: Genetic characterization of polypeptide deformylase, a distinctive enzyme of eubacterial translation. EMBO J. 13 (1994) 914-923). Whereas deletion of the fmt gene alone leaves the mutant bacteria viable, deletion of the def gene alone as well as re-introduction of the fmt gene into a def-fmt background is lethal (Mazel, D., Pochet, S. and Marliere, P.: Genetic characterization of polypeptide deformylase, a distinctive enzyme of eubacterial translation. EMBO J. 13 (1994) 914-923), demonstrating that essential bacterial proteins either have to be deformylated, and/or that the initiator methionine has to be cleaved off in order to render these proteins functional.

For the purpose of the present invention, a def-fmt deletion mutant was selected for enhanced growth rates under permanent proliferation in minimal medium at 37° C. until its growth rate approximated that of the parent wild-type bacterium.

For a second application; the def-fmt deletion mutant previously selected for growth at 37° C. was selected for enhanced growth rates under permanent proliferation in minimal medium at 42° C. until its growth rate approximated that of the parent wild-type bacterium.

eubacterium with altered translational mechanism such that it contains no fmt and def genes yet grows at wt (wild-type) rate.

*E. coli* formyl-free strain growing at temperatures higher than 37° C.

use of such strains for expression of recombinant proteins.

use of such strains for production of any product in *E. coli* which must not be contaminated with N-formylated peptides.

EXAMPLES

1. Selection of enhanced growth rate in the def-fmt mutant (figure).

2. Growth rate of evolved strains at 30° C., 37° C. and 42° C. in minimal medium and rich medium (table).

An *E. coli* strain for expression of N-formyl-free polypeptides. In eubacteria peptide synthesis is initiated at methionine start codon which are read by N-formyl methionine tRNA. Prior to translation initiation the methionyl moiety of the charged tRNA is N-formylated by the action of Met-tRNAi transformylase. The N-formyl group is removed from the native protein by polypeptide deformylase, and the initiator methionine can then be cleaved off by methionine aminopeptidase, completing the primer methionine cycle (FIG. 1a). In contrast, archaea and eukaryotes have a primer methionine cycle devoid of N-formylating and deformylating activities (FIG. 1b).

Expression of eukaryotic proteins in eubacterial hosts often results in the production of recombinant proteins that retain an N-terminal formylmethionyl residue. Since N-formylated peptides are highly immunogenic, incomplete deformylation precludes, for example, their use for therapeutic purposes. Several approaches to circumvent this problem have been proposed, e.g., expression in the presence of trimethoprim and thymidine (Sandman, K., Gryling, R. A. and Reeve, J. N. (1995): Improved N-terminal processing of recombinant proteins synthesized in *Escherichia coli*. Biotechnology 13, 504-506 or overexpression of peptide deformylase in the host (Warren, W. C., Bentle, K. A., Schlittler, M. R., Schwane, A. C., O'Neil, J. P. and Bogosian, G. (1996): increased production of peptide deformylase eliminates retention of formylmethionine in bovine somatotropin overproduced in *Escherichia coli*. Gene 174, 235-238).

The inventors have opted for a radical solution, simplifying the primer methionine cycle in *Escherichia coli* by deletion of the def-fmt operon that encodes polypeptide deformylase and met-tRNAi transformylase, and improving the resulting, crippled strain, by selecting for increasing growth rates (and therefore improved rates of protein synthesis) under permanent proliferation in suspension. The inventors have isolated the def and fmt genes from *E. coli* and created a deletion mutant (D[def-fmt]) devoid of both genes (Mazel, D., Pochet, S. and Marliere, P. (1994): Genetic characterization of polypeptide deformylase, a distinctive enzyme of eubacterial translation. EMBO J. 13, 914-923). The resulting strain was found to be viable, however its growth rate was dramatically reduced, from 0.9 per h to 0.25 per h in minimal medium at 37° C.

Protein synthesis in living cells is dependent on the concerted action of a complex assembly of the protein and rRNA constituents of ribosomes and a host of factors catalyzing aminoacylation of tRNAs, initiation, elongation and termination of translation as well as maturation of nascent polypeptides. N-terminal formylation is among the most conserved features that distinguish eubacteria from archaea and eukaryotes. Removing the enzymes that catalyze the corresponding reactions is therefore expected to remove the efficiency of protein synthesis far from its wild-type optimum. Evolutionary resurrection from this type of genetic injury will require multiple adaptive mutations to render the bacterial translation machinery more similar to that found in eukaryotes. State-of-the-art technologies for directed evolution ex vivo are unable to predict and select the adaptive mutations that would re-establish wild-type protein synthesis rates in a D(def-fmt) background.

Figure 2A:
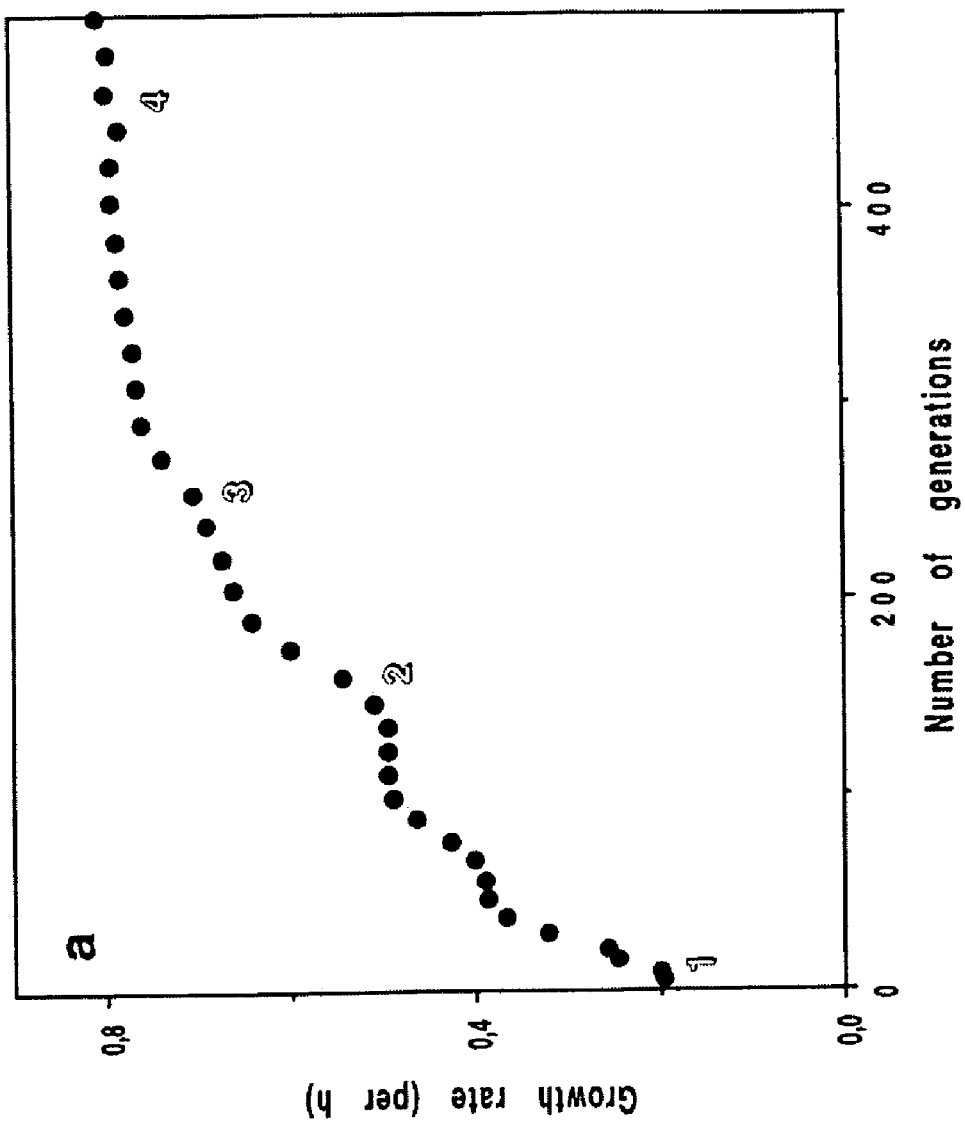
(FIG. 2*a*) Cells were kept under permanent proliferation in minimal medium at 37° C. A turbidostat regime at 5×10$^8$ cells/ml was applied. Growth rates are averaged over 24 h periods. Two independent runs are shown.
Figure 2B:
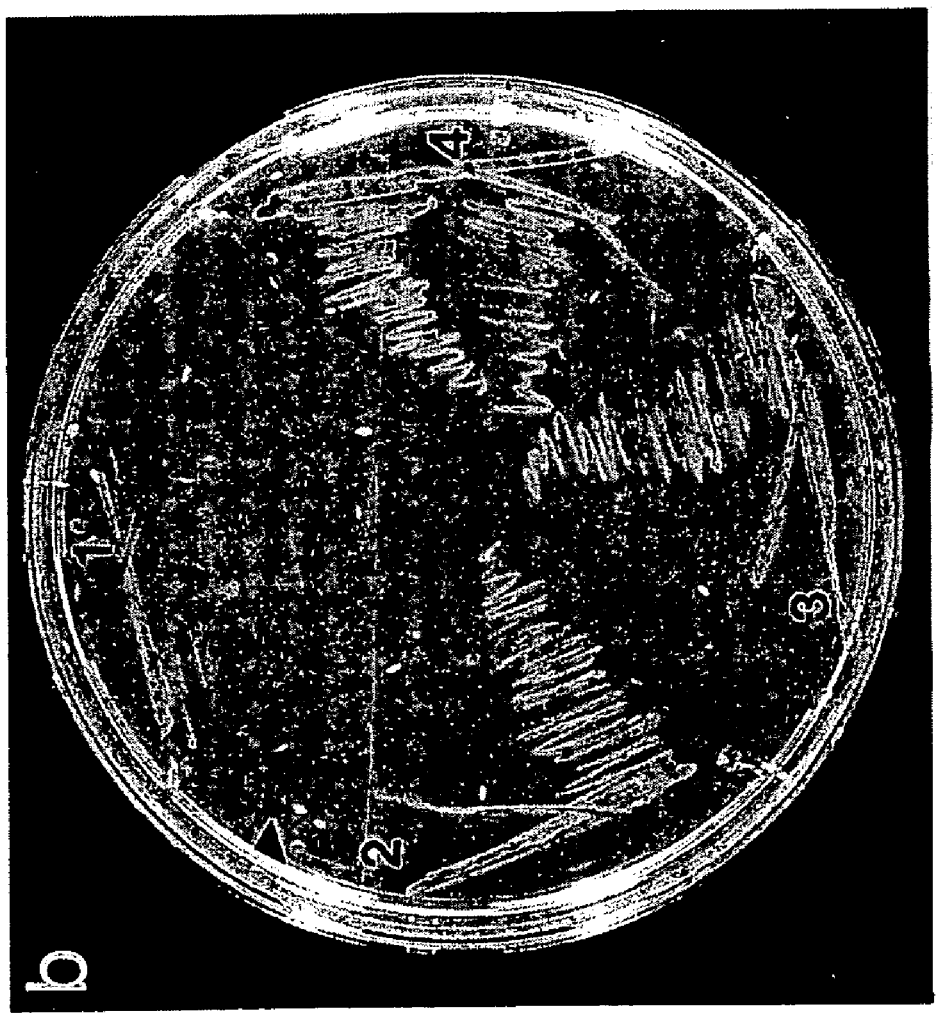
(FIG. 2*b*) Input (1) and evolved strains isolated during the process (2, 3, 4; c.f., numbers and open circles in a) were grown on minimal agar for 36 h at 37° C.

In vivo evolution of the D(def-fmt) mutant under permanent proliferation in suspension in a turbidostat regime yields variants with increasing growth rate; approximating wild-type growth rate after about 1 month (ca. 300 generations) of permanent selection (FIG. 2a). FIG. 2b shows drastically increased biomass production of evolved derivatives tested for growth on minimal agar as compared to the input D(def-fmt) mutant. Stepwise increases in the growth rate of the evolving population suggest selection and fixation of successive adaptive mutations. The inventors have evidence that the protein met-tRNA synthetase, certain ribosomal proteins, initiation factor 2, and methionine aminopeptidase are altered in the output strains.

Figure 3:
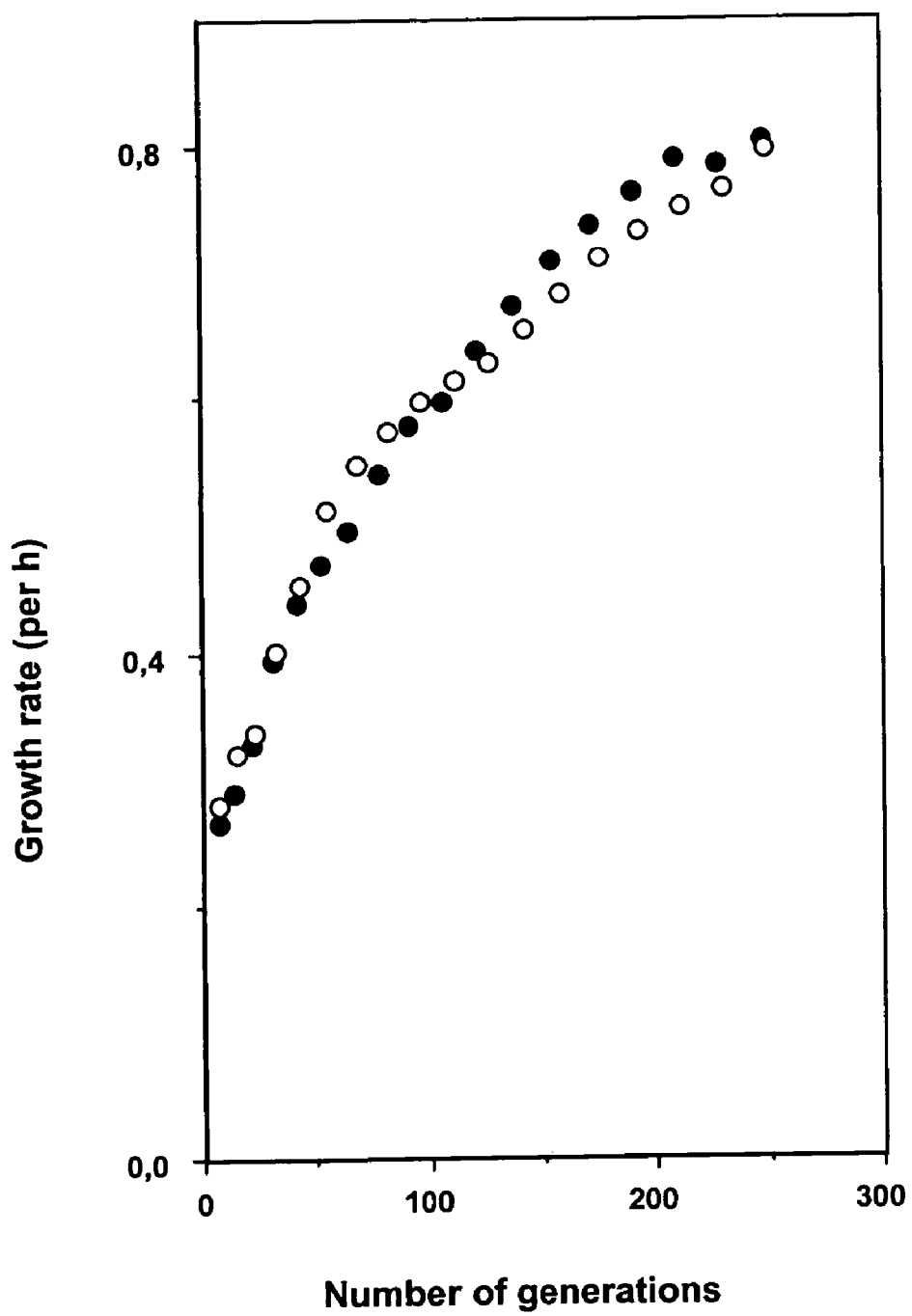
FIG. 3: In vivo evolution of a D(def-fmt) mutant at increased mutation rates. Two independent runs are shown.

The evolutionary process can be accelerated by increasing variation in the population (FIG. 3). When mutation rates in the population under selection were increased by a factor of about 1,000, wild-type growth rates were approximated within about half the time required for the process shown in FIG. 2a.

Current technology for continuous proliferation of cells in suspension suffers a major drawback, selection of adhesive variants which stick to inner surfaces of the device and escape the selective pressure imposed by continuous or conditional dilution (Chao, L. and Ramsdell, G. (1985): The effects of wall populations on coexistence of bacteria in the liquid phase of chemostat cultures. J. Gen. Microbiol. 131, 1229-1236). In principle, this can be avoided by serial subculture of cells in suspension (Lenski, R. E. and Travisano, M. (1994): Dynamics of adaptation and diversification: A 10,000-generation experiment with bacterial populations. Proc. Natl. Acad. Sci. USA 91, 6808-6814), a technique where cells in suspension are frequently transferred into fresh culture vessels (i.e., surfaces are periodically discarded), creating a selective disadvantage for static variants. At an industrial scale, serial subculture technology has not been systematically exploited because it is laborious and requires absolute sterility during transfers.

Figure 4A:
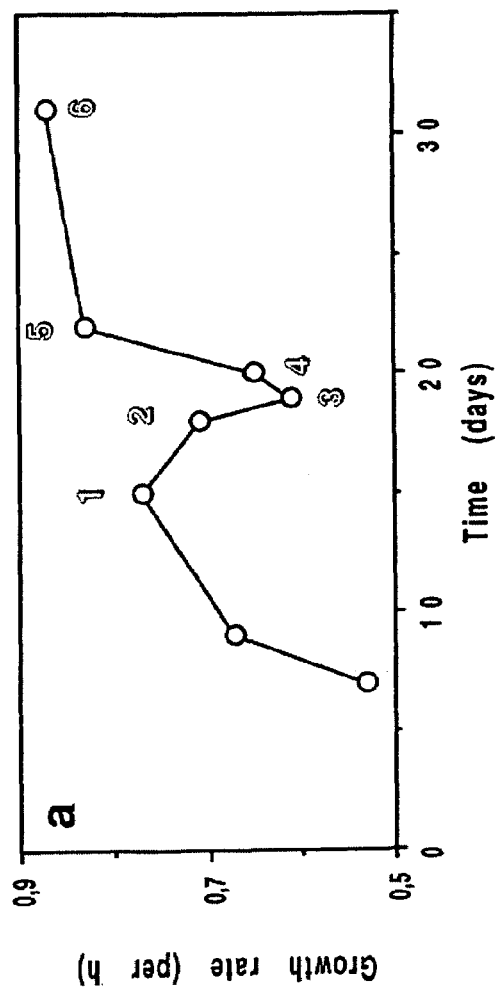
(FIG. 4*a*) Growth rates of the populations as measured in batch culture.
Figure 4B:
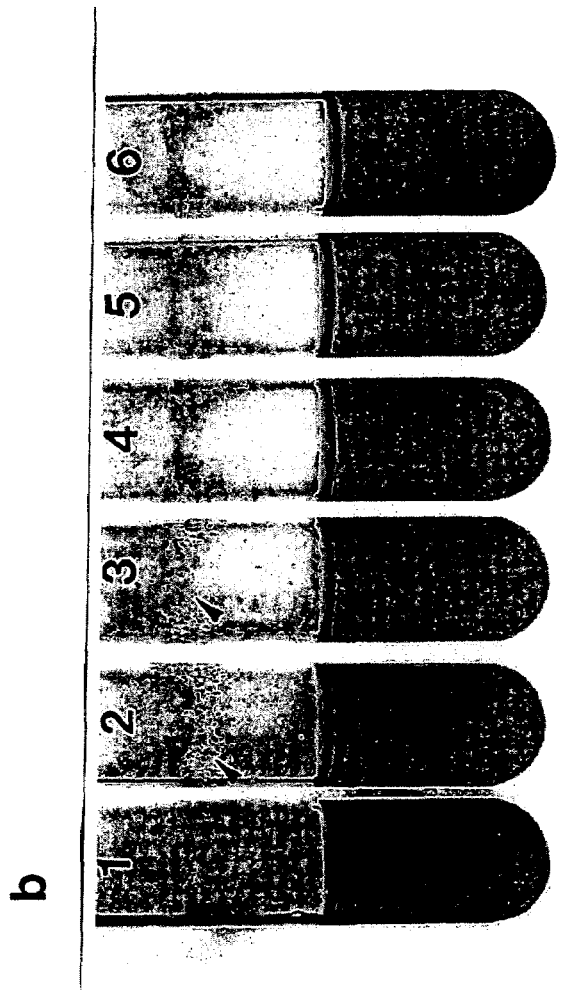
(FIG. 4*b*) Adhesion of cell material to glass surfaces. Isolates (points 1-6 in a) were cultivated in glass tubes for 20 h at 37° C. Arrowheads point to material that accumulated on the surface during cultivation.

FIG. 4: automated technology for the permanent proliferation of populations of cells exclusively in suspension. During the course of an experiment similar to that shown in FIG. 3, operation of the device was manipulated such that static, adhesive variants were no longer destroyed and could freely compete with cells in suspension. Highly adhesive variants accumulated rapidly (FIG. 4b). In parallel, the growth rate of the population decreased, demonstrating that these static variants are not subject to the selective pressure imposed on the cells in suspension. When proper operation of the device was re-established, these variants were rapidly and effectively eliminated from the evolving population.

The automated device describe in PCT WO 00/34433 is the first operational apparatus which allows permanent proliferation of living cells under defined, selective conditions.

The automated process frequently and effectively destroys static variants in any part of the device, overcoming the primary obstacle to continuous proliferation of cells in suspension for indefinite periods of time.

The inventors have created derivatives of *Escherichia coli* with a primer methionine cycle similar to that in eukaryotic cells. The strains will allow for expression of N-formyl-free polypeptides in *E. coli*.

Evolved microbial strains with unique genetic and metabolic imprints will serve as ancestors for the diversification of lines of industrially fit microorganisms.

Our reference strain is γ2045: *Escherichia coli* MG1655 Δ(def-fmt):: cat, dnaQ::miniTn10 [CMR$^R$, Tc$^R$].

MG 1655 is a wild-type K12 strain of *E. coli* (see EMBO J. (1994) 13:914-923). Δ(def-fmt) means deletion of the def-fmt operon, which encodes the polypeptide deformylase and the Met-tRNAi transformylase activities. This allele has been described (EMBO J. (1994) 13:914-923).

The writing::cat means the insertion of a cat (chloramphenicol acetyl-transferase) germ in the Δ(def-fmt) locus dnaQ::miniTn10 means that the dnaQ gene (epsilon subunit of the DNA polymerase, the proof-reading subunit) is interrupted by the insertion of a minitransposon Tn10 which confers the tetracycline resistance [CmR, TcR] means that the strain is resistant to chloramphenicol (25 micg/ml) and to Tetracycline (15 micg/ml).

This bacterial strain carries a deletion of the def-fmt operon and is consequently defective in the Met-tRNAi transformylase and polypeptide deformylase activities. This strain also carries dnaQ mutation and consequently shows a mutator phenotype. This strain is a derivative of β2124 that has been selected to grow in minimal and complex nutrient media at 30° C., 37° C. and 42° C. with near wild-type rate (approximately 25 min in LB and approximately 80 min in MS minimal medium (Richard (1993), J. Biol. Chem. 268:26827-26835) with mannitol as carbon source at final concentration 0.2% at 37° C.). The original β2124 strain shows a growth rate of approximately 200 min in MS minimal medium+mannitol at 37° C. γ2045, the 2124 derivative, was selected for enhanced growth rates under permanent proliferation in minimal medium at 37° C. until its growth rate reached that of MG 1655, the parent wild-type bacterium.

The mutator phenotype can be rescued by complementation with a dnaQ wild type allele expressed either from a plasmid or from the chromosome, through an allele replacement in γ2045.

Subject: β2137. Our reference strain is 2137: *Escherichia coli* MG1655, Δfmt::cat [44°CS, CmR] MG1655 is a wild-type K12 strain of *E. coli* (see EMBO J. (1994) 13:914-923). Δfmt means deletion of the fmt gene which encodes the Met-tRNAi transformylase activity. This allele has never been described, it is a Pst I deletion, internal to fmt (nucleotides 247 to 484).

The writing::cat means the insertion of a cat (chloramphenicol acetyl-transferase) gene at the PstI site of the deletion.

The cat gene is identical to the one used for the construction of the (def-fmt)::cat allele (see EMBO J. (1994) 13:914-923).

[44 CS, CmR] means that the strain is thermosensitive and resistant to chloramphenicol (25 micg/ml).

This bacterial strain carries a deletion of the fmt gene and is consequently defective in the Met-tRNAi transformylase activity.

This strain is a derivative of MG1655 that has a growth rate of approximately 200 min in MS minimal medium+mannitol at 37° C.

The invention claimed is:

1. A recombinant eubacterial cell, which contains a polynucleotide encoding an exogenous polypeptide, that has been modified to lack a functional def gene or a functional fmt gene, or both;
   wherein said modified recombinant eubacterial cell expresses the exogenous polypeptide as a non-formylated polypeptide, and
   wherein the corresponding unmodified recombinant eubacterial cell, which contains a functional def gene or a functional fmt gene, or both, expresses the exogenous polypeptide as a formylated polypeptide.

2. The modified eubacterial cell of claim 1 which has been modified to inactivate or delete the fmt (Met-tRNA transformylase) gene.

3. The modified eubacterial cell of claim 1, which has been modified by inactivating or deleting both the def (deformylase) and fmt (Met-tRNA transformylase) genes.

4. The modified eubacterial cell of claim 1 that is *Escherichia*.

5. The modified eubacterial cell of claim 1, which lacks deformylase activity.

6. The modified eubacterial cell of claim 1, which lacks deformylase and Met-tRNA transformylase activity.

7. The eubacterial cell of claim 1, wherein the growth rate of said cell at 37° C. is at least equivalent to the growth rate of a corresponding bacterial cell not having said fmt or def-fmt deletion(s).

8. The modified eubacterial cell of claim 1, wherein the growth rate of said cell at 42° C. is at least equivalent to the growth rate of a corresponding bacterial cell not having said fmt or def-fmt deletion(s).

9. A method of producing a non-formylated protein, polypeptide and/or peptide comprising:
   cultivating the modified eubacterial cell of claim 1 for a time and under conditions suitable for expression of a non-formylated protein, polypeptide and/or peptide, and, optionally,
   recovering or isolating said non-formylated protein, polypeptide and/or peptide.

10. The method of claim 9, wherein said modified eubacterial cell is cultivated at 37° C.

11. The method of claim 8, wherein said modified eubacterial cell is cultivated at 42° C.

12. An isolated or purified *Escherichia coli* that has been modified to lack a functional def gene or a functional fmt gene, or both, and which expresses at least one exogenous polypeptide that is not formylated;
   wherein said exogenous polypeptide when expressed by the corresponding unmodified recombinant *Escherichia coli* is formylated.

13. The isolated or purified *Escherichia coli* of claim 12, which lacks deformylase activity.

14. The isolated or purified *Escherichia coli* of claim 12, which lacks deformylase and Met-tRNA transformylase activity.

15. The isolated or purified *Escherichia coli* of claim 12, which has a growth rate at 37° C. which is at least equivalent to the growth rate of a corresponding isolated or purified *Escherichia coli* not having said fmt or def-fmt deletion(s).

16. The isolated or purified *Escherichia coli* of claim 12, which has a growth rate at 42° C. which is at least equivalent to the growth rate of a isolated or purified *Escherichia coli* not having said fmt or def-fmt deletion(s).

17. A method of producing a non-formylated protein, polypeptide and/or peptide comprising:
   cultivating the modified *Escherichia coli* of claim 12 for a time and under conditions suitable for expression of a non-formylated protein, polypeptide and/or peptide, and recovering or isolating said non-formylated protein, polypeptide and/or peptide.

18. The method of claim 17, wherein said modified *Escherichia coli* is cultivated at 37° C.

19. The method of claim 17, wherein said modified *Escherichia coli* is cultivated at 42° C.

* * * * *